United States Patent [19]

Totani et al.

[11] Patent Number: 4,560,781

[45] Date of Patent: Dec. 24, 1985

[54] GLYCOLIC ACID PLATINUM COMPLEXES

[75] Inventors: Tetsushi Totani, Hyogo; Katsutoshi Aono, Nara; Michihiro Komura, Hyogo, all of Japan

[73] Assignee: Shionogi & Co., Ltd., Osaka, Japan

[21] Appl. No.: 552,906

[22] Filed: Nov. 17, 1983

[30] Foreign Application Priority Data

Dec. 21, 1982 [JP] Japan .................................. 57-225272

[51] Int. Cl.⁴ .............................................. C07F 15/00
[52] U.S. Cl. ....................................... 556/137; 514/492
[58] Field of Search ......................... 260/429 R, 429 J

[56] References Cited

U.S. PATENT DOCUMENTS

| | | | |
|---|---|---|---|
| 4,225,529 | 9/1980 | Hydes et al. | 260/429 R |
| 4,230,631 | 10/1980 | Hydes et al. | 260/429 R |
| 4,250,189 | 2/1981 | Hydes et al. | 260/429 R X |
| 4,271,085 | 6/1981 | Amundsen et al. | 260/429 R |
| 4,359,425 | 11/1982 | Totani et al. | 260/429 R |
| 4,466,924 | 8/1984 | Verbeek et al. | 260/429 R |

OTHER PUBLICATIONS

Chemical Abstracts, 92, 88521d; 92, 51723v, (1980).
Chemical Abstracts, 93, 125662u, (1980); 93, 125663v, (1980).
Chemical Abstracts, 78, 105899p, (1973).
Chemical Abstracts, 80, 66593d, (1973).

Primary Examiner—Helen M. S. Sneed
Attorney, Agent, or Firm—Wenderoth, Lind & Ponack

[57] ABSTRACT

Novel water-soluble glycolic acid platinum complexes which have more potent antitumor activity with lower nephrotoxicity than cisplatin are provided.

They can be administered parenterally to mice attacked by malignant tumors.

Prepared from dinitrato-platinum complexes of amines on treatment with anion exchange resins and subsequent reaction with glycolic acid.

7 Claims, No Drawings

GLYCOLIC ACID PLATINUM COMPLEXES

BACKGROUND OF THE INVENTION

1. Field of the Invention

The present invention relates to novel glycolic acid platinum complexes which have antitumor activity comparable to or more potent than that of cisplatin. The nephrotoxicity is very low.

2. Description of the Prior Art

The analogous compounds of cisplatin [Japanese Unexamined Patent Publication No. 49-7224, Bristol-Myers Co.] have been investigated since its potent antitumor activity has been observed; as the result of the fact, the compounds such as malonato(1,2-diaminocyclohexane)platinum(II) [Japanese Unexamined Patent Publication No. 53-31648], sulfato(1,2-diaminocyclohexane)platinum(II) [Japanese Unexamined Patent Publication No. 54-44620], 4-carboxyphthalato(1,2-diaminocyclohexane)platinum(II) [Japanese Unexamined Patent Publication No. 54-46752], cis-dichloro-trans-dihydroxy-bis(isopropylamine)platinum(IV) [Japanese Unexamined Patent Publication No. 57-77694], and the like have been investigated. The present inventors have also investigated analogous compounds of cisplatin and they have found various type of platinum complexes having potent antitumor activity and high water solubility, for example, bicycloheptane platinum complexes [Japanese Unexamined Patent Publication No. 58-79933], adamantane platinum complexes [Japanese Unexamined Patent Publication No. 58-79994], 1,2-cyclohexanediamine platinum complexes [Japanese Unexamined Patent Publication No. 58-124797], and other platinum complexes [Japanese Unexamined Patent Publication Nos. 56-154493 and 57-123198].

BRIEF SUMMARY OF THE INVENTION

The present invention relates to novel glycolic acid platinum complexes. More particularly, it relates to the compounds represented by the following general formula (I):

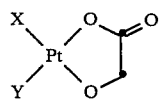

[wherein X and Y each is straight or branched chain alkylamine, or X and Y taken together form ethylenediamine, 1,2-diaminocyclohexane, exo-cis-2,3-diaminobicyclo[2.2.1]heptane, or 1,2-diaminoadamantane].

The compounds (I) are prepared according to the following reaction sequence.

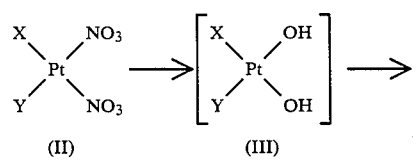

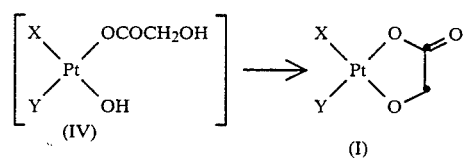

The compounds (I) are useful as parenterally administrable antitumor agents with low nephrotoxicity.

DETAILED DESCRIPTION OF THE INVENTION

The present invention relates to novel glycolic acid platinum complexes. More particularly, it relates to the compounds represented by the following general formula (I):

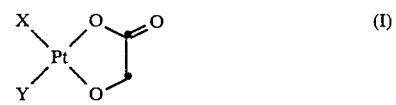

[wherein X and Y each is straight or branched chain alkylamine, or X and Y taken together form ethylenediamine, 1,2-diaminocyclohexane, exo-cis-2,3-diaminobicyclo[2.2.1]heptane, or 1,2-diaminoadamantane]

The meanings of the terms used in the above definition are shown below:

the straight or branched chain alkylamine includes those of 1–5 carbon atoms, for example methylamine, ethylamine, propylamine, isopropylamine, butylamine, isobutylamine, t-butylamine, pentylamine, isopentylamine, t-pentylamine, neo-pentylamine, and the like.

The compounds (I) of the present invention can easily be prepared according to the following reaction sequence.

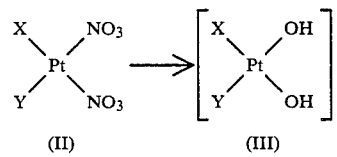

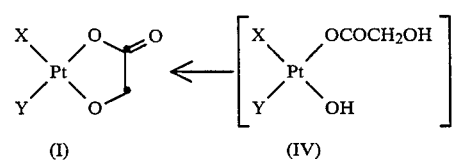

[wherein X and Y each has the same significance as defined above].

In the reaction sequence described above, an aqueous solution of the compounds (II) is passed through a column of an anion exchange resin (OH type) such as Amberlite IRA-400 (Rohm & Haas Co.), Dowex I (Dow Chemical Co.), Daiaion SA-10A (Mitsubishi Chemical Industries Ltd.) to give the compounds (III) in which the two nitrato groups are replaced by hydroxy groups. Preferably, the resulting compounds (III) are usually used as the solution separated above in the next step since these compounds are unstable in solid form.

An aqueous solution of the compounds (III) is allowed to react with addition of glycolic acid to give the desired compounds (I) of the present invention, probably through the intermediate compounds (IV).

The reaction of the compounds (II) into the compounds (III) proceeds quantitatively, so glycolic acid may be used in an equivalent amount to the compounds (II). The reaction is usually carried out at room temperature and takes 10 days for completion; if necessary the reaction may be conducted at an elevated temperature of 50°–70° C.

The starting compounds (II) described in the above reaction sequence are known, or obtained by the reaction of the known compounds represented by the following general formula:

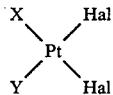

[wherein X and Y each has the same significance as defined above; Hal is halogen] with silver nitrate.

The halogen mentioned above means chlorine, bromine, and iodine.

The compounds of the present invention may sometimes take polymeric forms, for example, a dimer structure as shown below.

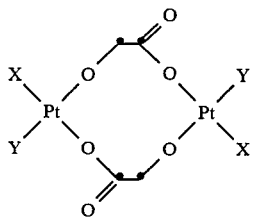

[wherein X and Y each has the same significance as defined above].

The compounds of the present invention have an antitumor activity comparable to or more potent than that of cisplatin and show lower nephrotoxicity. Further, they can easily be administered parenterally to patients attacked by malignant tumors since they are highly soluble in water. For example, the compounds (I) dissolved or suspended in proper solvents for injection (e.g., distilled water for injection, physiological saline, 5% glucose aqueous solution, aqueous ethanol, aqueous glycerin, and aqueous propylene glycol) can be administered intravenously, intramuscularly, or subcutaneously, or by means of instillation. The compounds (I) may be placed in closed ampoules as a solution or a suspension, and more preferably preserved in ampoules or vials in solid forms of crystals, powders, fine crystals, lyophilizate, so as to be dissolved immediately before use. Stabilizer may also be added.

When the compounds (I) are used in the treatment of tumors of adults, they are parenterally administered at a dose or doses of 100 to 500 mg/day, usually 1 to 3 times a day.

The compounds provided by the process of this invention are exemplified below:

Glycolato[exo-cis-2,3-diaminobicyclo[2.2.1]heptane]-platinum(II),
Glycolato(1,2-diaminoadamantane)platinum(II),
Glycolato(cis-1,2-diaminocyclohexane)platinum(II),
Glycolato(trans-d-1,2-diaminocyclohexane)platinum-(II),
Glycolato(trans-l-1,2-diaminocyclohexane)platinum-(II),
Glycolato(1,2-diaminoethane)platinum(II),
Glycolato[cis-bis(methylamine)]platinum(II), and the like.

The present invention will be explained in more detail by the following Examples and Experiments.

EXAMPLE 1

Glycolato[exo-cis-2,3-diaminobicyclo[2.2.1]heptane]-platinum(II)

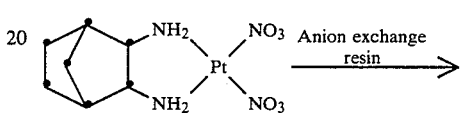

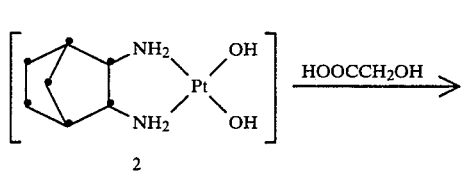

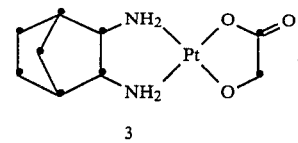

The known compound 1 (267 mg, 0.60 mmol) [Japanese Unexamined Patent Publication No. 56-154493] is treated with an anion exchange resin Daiaion SA-10A (OH type), and to 20 ml of the resulting aqueous solution of the compound 2 is added 76 mg (0.60 mmol) of glycolic acid in small portions with stirring, and the mixture kept at room temperature overnight. The solution is concentrated at 50° C. or lower, and the resulting light brown solid is dissolved in a minimum amount of water (less than 5 ml) with warming, and the solution is allowed to crystallize gradually in a desiccator (containing calcium chloride as dryer). After 3 days, the precipitating colorless crystals are collected by filtration, washed with a small amount of water and methanol, and dried in vacuum at 100° C. to give 130 mg (yield: 74%) of the titled compound 3.

m.p. higher than 225° C. (decomp.)

Elemental analysis (for $C_9H_{16}N_2O_3Pt$): Calcd. (%): C, 27.34; H, 4.08; N, 7.09; Pt, 49.35. Found. (%): C, 27.80; H, 4.25; N, 7.39; Pt, 49.00.

IR: $\nu_{max}^{Nujol}$ 3230(m), 3200(sh), 3050(m), 1640(s), 1600(m), 1340(s), 1320(m), 1260(w), 1240(w), 1155(w), 1065(m), 1060(m), 920(w), 830(w), 760(w) cm$^{-1}$.

$^1$HNMR: (in $D_2O$, ppm from TMS as the external standard, $\delta$) 1.35–2.10, 2.72, 2.82, 3.40 (norbornyl group), 4.47 (glycolato —$CH_2$—, $J_{195Pt-H}=34$ Hz).

EXAMPLE 2

Glycolato(1,2-diaminoadamantane)platinum(II)

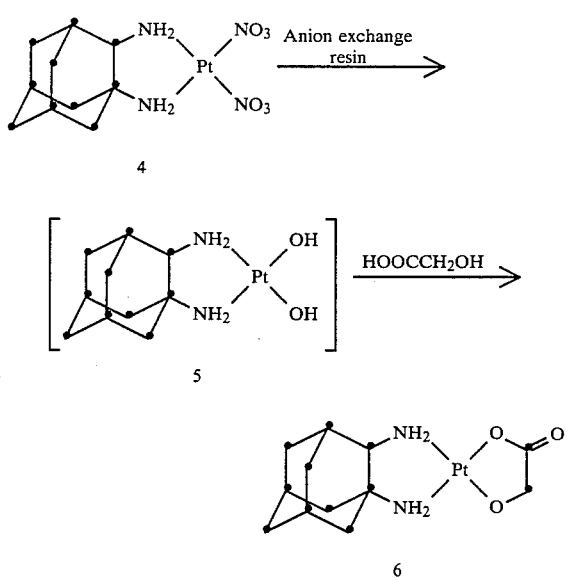

The compound 4 (1.1 mmol) [Japanese Unexamined Patent Publication No. 58-79994] is treated with an anion exchange resin Daiaion SA-10A (OH type), and to the resulting aqueous solution of the compound 5 is added 83 mg (1.1 mmol) of glycolic acid, and the mixture kept at room temperature for 24 hours. In the same manner as in Example 1, the compound 6 produced as crude crystals is recrystallized from water to give 320 mg (yield: 69%) of the titled compound 6.

m.p. higher than 220° C. (turn dark without melting)

Elemental Analysis (for $C_{12}H_{20}N_2O_3Pt$): Calcd. (%): C, 33.10; H, 4.63; N, 6.43; Pt, 44.80. Found. (%): C, 32.43; H, 4.66; N, 6.60; Pt, 44.69.

IR: $\nu_{max}^{Nujol}$ 3400(m), 3180(s), 3100(s), 1620(s), 1300(m), 1210(w), 1160(w), 1080(w), 1050(m), 920(w), 760(w), 720(w) cm$^{-1}$.

$^1$HNMR: (in $D_2O$, ppm from TMS as the external standard, δ), 1.75–1.95 (adamantyl group $C_3$–$C_{10}$—H, 13H), 3.15 (adamantyl group $C_2$—H, 1H), 4.49 (glycolato —$CH_2$—, 2H, $J_{195-H}=34$ Hz).

EXAMPLE 3

Glycolato(cis-1,2-diaminocyclohexane)platinum(II)

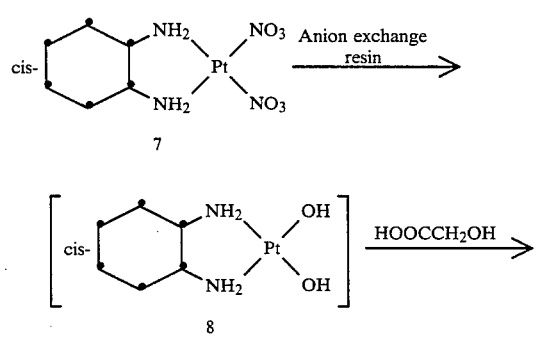

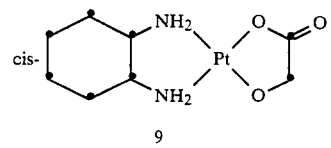

The compound 7 [Japanese Unexamined Patent Publication No. 54-44620] (2.95 g, 6.81 mmol) is dissolved in 50 ml of water with heating, and the resulting solution is cooled, and passed through a column of an anion exchange resin Daiaion SA-10A (OH type). The eluted solution of the compound 8 is dissolved in 533 mg (7.01 mmol) of glycolic acid.

The reaction mixture is stirred for about 10 minutes, concentrated to 4 ml, and kept over silica-gel in a desiccator at room temperature for 11 days. Further, the mixture is purified by chromatography with silica-gel. The eluate with ethanol-$H_2O$ (5:1) is evaporated to give crystals which are recrystallized from ethanol-$H_2O$ (5:1) to give 836 mg (yield: 32%) of the titled compound 9 as slightly yellow crystals.

m.p. higher than 217° C. (decomp.).

Elemental Analysis (for $C_8H_{16}N_2O_3Pt \cdot \frac{1}{2}H_2O$): Calcd. (%): C, 24.49; H, 4.36; N, 7.14; Pt, 49.72. Found. (%): C, 24.48; H, 4.28; N, 7.43; Pt, 50.59.

IR: $\nu_{max}^{Nujol}$ 3170(m), 3055(w), 1605(s), 1435(w), 1355(w), 1318(w), 1285(w), 1260(w), 1245(w), 1230(m), 1167(w), 1135(m), 1100(w), 1080(w), 1060(m), 1035(w), 980(w), 935(w), 880(w), 845(w), 830(w), 770(w), 720(m) cm$^{-1}$.

$^1$HNMR: (in $D_2O$, ppm from TMS as the external standard, δ) 1.73–2.53, 2.93–3.90 (broad, cyclohexyl group 10H), 4.50 (s, 2H, satellite $J_{195-H}=33$ Hz, —$CH_2$—).

EXAMPLE 4

Glycolato(trans-l-1,2-diaminocyclohexane)platinum(II)

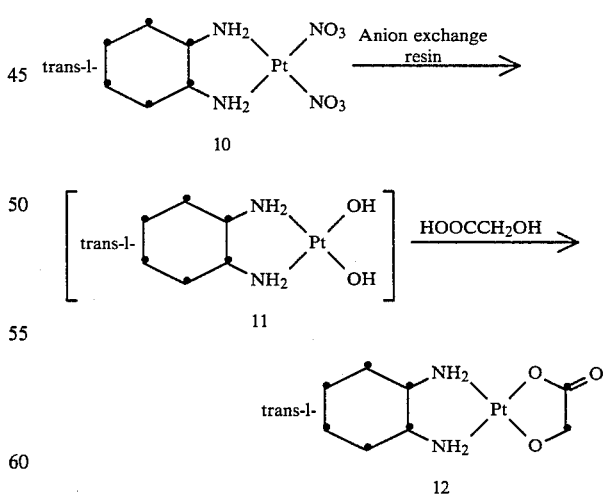

The compound 10 [Japanese Unexamined Patent Publication No. 54-44620] (2.02 g, 4.66 mmol) is converted into the compound 11 by an anion exchange resin. To an aqueous solution of the compound 11 is added 355 mg (4.67 mmol) of glycolic acid, and the mixture is stirred for 1 hour, and concentrated at 50° C.

or lower. The yellow solution containing fine crystals precipitated is kept over silica-gel as dryer in a desiccator for 12 days. This solution is ice-cooled enough to yield crystals, which are collected by filtration. Recrystallized from water and dried in vacuum at room temperature to give 1.08 g (yield: 60%) of the titled compound 12. m.p. 223°–226° C. (decomp.)

Elemental Analysis (for $C_8H_{16}N_2O_3Pt$): Calcd. (%): C, 25.07; H, 4.21; N, 7.31; Pt, 50.90. Found. (%): C, 24.41; H, 4.19; N, 7.31; Pt, 50.63.

IR: $\nu_{max}^{Nujol}$ 3400(w), 3180(w), 3090(w), 1615(m), 1365(m), 1325(m), 1310(m), 1263(w), 1180(m), 1065(s), 1035(m), 920(m), 760(w), 720(m) cm$^{-1}$.

$^1$HNMR: (in $D_2O$, ppm from TMS as the external standard, δ) 1.42–3.10 (broad, cyclohexyl group, 10H), 4.52 (glycolato —$CH_2$—, 2H, $J_{195Pt-H}$=33.6 Hz).

EXAMPLE 5

Glycolato(1,2-diaminoethane)platinum(II)

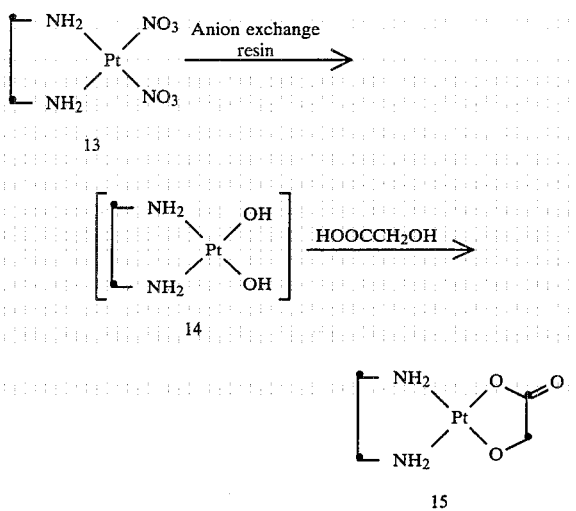

An aqueous solution of the compound 13 (0.79 mmol) prepared from the known compound cis-dichloro(1,2-diaminoethane)platinum(II) (J. Am. Chem. Soc. 72 p.2433) on reaction with 2 equivalents of silver nitrate is passed through a column of an anion exchange resin Daiaion SA-10A (OH type). The eluted aqueous solution of the compound 14 to which is added 60 mg (0.79 mmol) of glycolic acid, is kept at room temperature for 3 hours. The solution is concentrated to about 1 ml at 45° C., and kept over silica-gel as dryer in a desiccator for 3 days. The resulting light yellow crystals are collected by filtration, washed with a small amount of chilled water, dried in vacuum at 60° C. to give 133 mg (yield: 51%) of the titled compound 15.

m.p. higher than 165° C. (decomp.).

Elemental Analysis (for $C_4H_{10}N_2O_3Pt$): Calcd. (%): C, 14.59; H, 3.06; N, 8.51; Pt, 59.26. Found. (%): C, 14.17; H, 2.96; N, 8.42; Pt, 59.85.

IR: $\nu_{max}^{Nujol}$ 3240(s), 3185(m), 1640(s), 1615(sh), 1375(sh), 1350(s), 1310(s), 1270(w), 1190(w), 1140(w), 1055(s), 1025(w), 1000(w), 920(m), 895(w), 755(m) cm$^{-1}$.

$^1$HNMR: (in $D_2O$, ppm from TMS as the external standard, δ) 3.00 (amine —$CH_2$—, 4H, $J_{195Pt-H}$=45 Hz), 4.52 (glycolato —$CH_2$—, 2H, $J_{195Pt-H}$=33 Hz).

EXAMPLE 6

Glycolato[cis-bis(methylamine)]platinum(II)

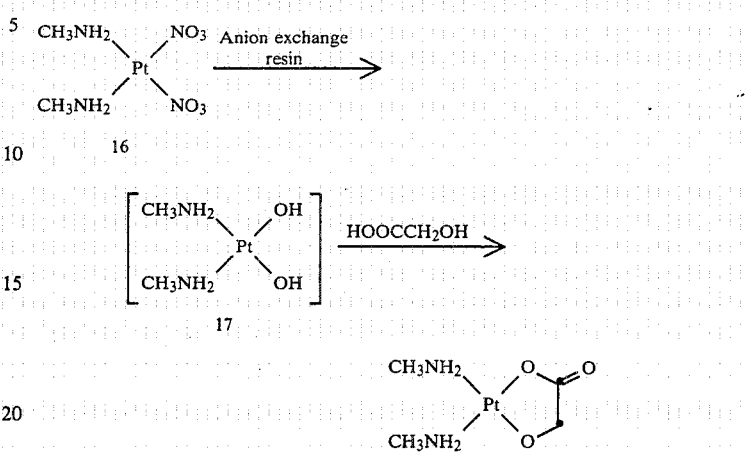

An aqueous solution of the compound 16 (1.5 mmol) prepared from the known compound cis-diiodo-bis(methylamine)platinum(II) [Bioinorg. Chem. 2, 187 (1973)] on reaction with 2 equivalent of silver nitrate is passed through a column of an anion exchange resin, Daiaion SA-10A (OH type). An aqueous solution of the resulting compound 17 to which is added 110 mg (1.4 mmol) of glycolic acid is kept at room temperature for 5 days. The solution is concentrated at 45° C., and the residual solid is washed with methanol to give 230 mg (yield: 44%) of the titled compound 18 as slightly yellow powder.

m.p. higher than 170° C. (decomp.).

Elemental Analysis (for $C_4H_{12}N_2O_3Pt$): Calcd. (%): C, 14.50; H, 3.65; N, 8.46; Pt, 58.90. Found. (%): C, 14.58; H, 3.69; N, 8.78; Pt, 59.08.

IR: $\nu_{max}^{Nujol}$ 3280(m), 3250(sh), 3100(m), 3050(m), 3010(sh), 1610(s), 1360(s), 1320(m), 1290(w), 1115(w), 1095(m), 1060(m), 1010(w), 925(m), 810(w), 780(w), 740(w), 720(w) cm$^{-1}$.

$^1$HNMR: (in $D_2O$, ppm from TMS as the external standard, δ) 2.84 (amine $CH_3$, $J_{CH_3-NH_2}$=6 Hz, $J_{195Pt-H}$=41 Hz), 2.86 (amine $CH_3$, $J_{CH_3-NH_2}$=6 Hz, $J_{195Pt-H}$=41 Hz), 4.55 (glycolato —$CH_2$—, $J_{195Pt-H}$=34 Hz) 4.20–6.0 ($NH_2$).

EXPERIMENT 1

Antitumor activity against L1210

Test method

Mouse Leukemia L1210 ascites cells ($10^5$ cells) are intraperitoneally inoculated to $BDF_1$ mice (7 to 10 mice are employed in each test group), and next day a predetermined amount of the test compounds is administered intraperitoneally. 5% Glucose solution is used as solvent for injection.

Test compound (A) Glycolato[exo-cis 2,3-diaminobicyclo[2.2.1]heptane]platinum(II)

(B) Glycolato(trans-l-1,2-diaminocyclohexane)platinum(II)

(C) Cisplatin

Evaluation of the Effect

From the average survival days (a) in the test group and those (b) of the untreated control group, the increase of lifespan (ILS) is calculated according to the following formula.

$$ILS (\%) = \frac{(a) - (b)}{(b)} \times 100$$

Result

| Dose (mg/kg) | ILS (%) | | |
|---|---|---|---|
| | (A) | (B) | (C) |
| 0 × 1 | — | — | — |
| 1 × 1 | 26 | 16 | |
| 2 × 1 | | 29 | 8 |
| 5 × 1 | 48 | 52 | 31 |
| 10 × 1 | >184 (3) | >103 (1) | >99 (1) |
| 20 × 1 | 108 | >165 (2) | −27 |
| 40 × 1 | −4 | 4 | |
| 80 × 1 | −31 | −43 | |

Note: The figure in parentheses ( ) means the number of mice survived for more than 30 days. (7 mice are employed in each test group, and 10 mice are employed only in control group).

What we claim is:
1. A compound of the general formula:

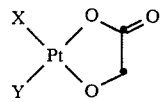

[wherein X and Y each is straight or branched chain alkylamine, or X and Y taken together form ethylenediamine, 1,2-diaminocyclohexane, exo-cis-2,3-diaminobicyclo[2.2.1]heptane, or 1,2-diaminoadamantane].

2. The compound claimed in claim 1, namely, glycolato[exo-cis-2,3-diaminobicyclo[2.2.1]heptane]-platinum(II).

3. The compound claimed in claim 1, namely, glycolato(1,2-diaminoadamantane)platinum(II).

4. The compound claimed in claim 1, namely, glycolato(cis-1,2-diaminocyclohexane)platinum(II).

5. The compound claimed in claim 1, namely, glycolato(trans-l-1,2-diaminocyclohexane)platinum(II).

6. The compound claimed in claim 1, namely, glycolato(1,2-diaminoethane)platinum(II).

7. The compound claimed in claim 1, namely, glycolato[cis-bis(methylamine)]platinum(II).

* * * * *